United States Patent [19]
Knox

[11] Patent Number: 4,761,159
[45] Date of Patent: Aug. 2, 1988

[54] METHOD OF CHEMICAL DEODORIZATION OF ARTICLES AND SOLUTIONS USED IN MEDICAL AND BIOLOGICAL PROCEDURES

[76] Inventor: Lewis Knox, 6587 Hiawatha, Chicago, Ill. 60646

[21] Appl. No.: 27,557

[22] Filed: Mar. 18, 1987

Related U.S. Application Data

[63] Continuation-in-part of Ser. No. 573,014, Jan. 23, 1984, Pat. No. 4,681,575.

[51] Int. Cl.$^4$ .................. A61F 2/60; A61F 13/16; A61F 2/66
[52] U.S. Cl. .................. 604/49; 604/359; 604/360; 604/333; 424/76.2; 424/76.21; 424/76.5; 424/76.6
[58] Field of Search ............... 424/76.1–76.9; 548/182, 190, 523, 532, 557; 604/27–29, 48, 49, 333, 359, 360

[56] References Cited

U.S. PATENT DOCUMENTS

| | | | |
|---|---|---|---|
| 3,172,817 | 3/1965 | Leupold et al. | 424/76 X |
| 4,160,020 | 7/1979 | Ayer et al. | 424/436 |
| 4,163,015 | 7/1979 | Johnson | 548/523 |

Primary Examiner—Richard J. Apley
Assistant Examiner—Alan W. Cannon
Attorney, Agent, or Firm—Michael G. Berkman

[57] ABSTRACT

A method of deodorizing articles, devices, and solutions involved in or used in medical and biological procedures including endoscopic procedures and associated solutions and materials. The method is to treat the materials and solutions to be deodorized with 2,5-hexanedione or with 2,3-pentanedione as a chemical deodorant. In a preferred treating composition the chemical deodorant is used as an aqueous solution containing a small amount of an essential oil-type masking agent and an oil solubilizing surfactant.

14 Claims, No Drawings

METHOD OF CHEMICAL DEODORIZATION OF ARTICLES AND SOLUTIONS USED IN MEDICAL AND BIOLOGICAL PROCEDURES

This application is a Continuation-in-Part of application Ser. No. 06/573,014, filed Jan. 23, 1984, now U.S. Pat. No. 4,681,575 and the entire disclosure of that application is hereby incorporated herein by reference to the extent it is not inconsistent herewith.

BACKGROUND OF THE INVENTION

This invention relates to the deodorization of solutions, articles, devices, and other equipment used in carrying out biological and medical procedures. More particularly, the invention is directed to a method for chemically deodorizing apparatus including medical instruments such as endoscopes, related equipment, and also the solutions and vessels used in conducting explorative medical and therapeutic procedures. The deodorization of rooms is also embraced in the method of the invention.

The invention itself is predicated on an unexpected and totally unpredictable discovery of a "new use" for known chemical compounds.

Many "deodorants" and deodorant preparations have been described for use to mask or cover-up objectionable or unpleasant odors derived from various sources. Some of these preparations have been designated for household use; others for use in industrial or manufacturing establishments. Still others have been promoted for use primarily in sick rooms, nursing homes, and in medical offices, examining and treatment rooms, and in hospitals.

For the most part, the prior art products employed have been dispensed as air-borne sprays, usually as vapors from pressurized aerosol containers.

The "deodorizing" formulations which have heretofore been used depend entirely upon "counter-acting" or blanketing the unpleasant odor. Other odor-producing materials, such as essential oils ("perfumes"), and functionally equivalent odoriferous preparations have been used to cover-up or mask the particular odor sought to be curtailed or eliminated.

None of the prior art products, preparations, or formulations deals directly with offending odor-producing material; none attacks the problem at its source. None acts directly on the chemical agent or agents which generate and are thus directly responsible for the offensive or otherwise objectionable odor. None "eliminates" the odor, but only covers it or masks it, temporarily at best. The results achieved have been far from satisfactory, and any "cover-up" achieved is short lived.

The present invention deals effectively with and resolves the problem described.

SUMMARY OF THE INVENTION

The present invention is based on the unexpected, surprising, unpredictable, and unobvious discovery that specific organic compounds may be used effectively as chemical deodorants. The term "chemical deodorant" as used herein is intended to portray the fact that the compounds identified and used in the method of the invention function to eliminate the objectionable odor by complexing, chelating, or by otherwise reacting chemically directly with the odor-producing agent. In this sense, the chemical deodorants of the invention are substantively different in kind and in function from the masking and the cover-up agents of the prior art.

While the exact nature and the precise mechanism of the critical reactions which occur in the practice of the invention are not presently known, the observed and demonstrated effect is unequivocal. The method of the invention is effective permanently to destroy the odor as well as the odor-generating capacity of the odoriferous metabolically produced organics with which the chemical deodorant of the invention comes into functional contact. It is an important feature of the method of the invention that the chemical deodorant is effective to eliminate odors derived from various sources including those derived from urine and from fecal matter.

Another important feature is that solutions containing the active chemical compound of the invention will not support bacterial growth; they are in this sense "self-sustaining".

Yet another feature of the odor-destroying compositions of the invention is that they are non-toxic in nature.

A related feature is that the chemical deodorant of the invention, as used in practicing the invention, is not a primary, a secondary, or a tertiary skin sensitizer.

A utilitarian feature of the method of the invention is that it is useful in eliminating odors derived from colon endoscopic procedures including odors from vacuum tanks and from recirculation tanks employed in such procedures.

A related feature of the invention is that it is useful in endoscopically-assisted urological and proctoscopic procedures.

Yet another important feature is that the chemical deodorant of the invention may be added to the water circulated in an endoscopic system without interfering with the efficacy of the procedure being carried out.

An important practical feature of the method of the invention is its versatility and its widespread utility. It has been found useful as a wash or rinse solution to deodorize apparatus and fixtures including sinks, commodes, bed pans and urinals. It also functions effectively as a spray to remove airborne odors in the ambient environment.

The above and other objects, features, and advantages of the invention will become more clearly understood upon a review of the following detailed description of preferred embodiments of the method of the invention. Such embodiments are presented here as examples only and are not to be considered as limiting the invention in any way.

DETAILED DESCRIPTION OF PREFERRED EMBODIMENTS

The present invention is predicated on the discovery that a specific organic compounds have the unique and unexpected and unpredictable capability of being used as chemical agents to destroy certain unpleasant and objectionable odors. The compounds used in practicing the method of the invention include acetonyl acetone which has the empirical formula $C_6H_{10}O_2$ and the structure

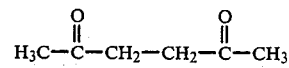

This compound, 2,5-hexanedione, is also known in the literature as $\alpha,\beta$-diacetyl ethane or 2,5-diketohexane.

A second compound found efficacious in the method of the invention is acetyl propionyl, having the empirical formula $C_5H_8O_2$ and the structure

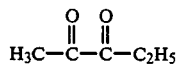

This compound is also known in the literature as 2,3-pentanedione, methyl ethyl glyoxal, or methyl ethyl diketone.

In accordance with the present invention, it has been found that, in contrast with prior widely used "cover-up" and "masking" preparations, the chemical deodorants of the invention function as viable chemical reactants in the odor-generating system into which they are introduced or to which they are physically applied. Rather than functioning as a "cover-up" or "mask" (by virtue of their own counter "essence," "scent,") the compounds as used in accordance with the method of the invention appear to chelate, or complex, or otherwise react with the odor-producing group or moiety of the odoriferous chemicals. The ultimate effect of this chemical interaction is to nullify or functionally to neutralize or to destroy the propensity of the material to release unpleasant odors.

The mode of application of the chemical deodorants of the invention to the articles, or devices, or media to be deodorized is not critical. In a preferred embodiment of the method of the invention, the chemical deodorant is used in the form of an aqueous solution in which the odor-destroying agent is present in a concentration in the range of from about 0.1 percent to about 8 percent by weight. For most applications a 2 percent solution is preferred.

In addition to the "active agent," it has been found advantageous, for some applications, to include a small concentration, in the order of 0.05 to 0.5 percent by weight of an aromatic essential oil or "perfume" to impart a pleasant aroma to the treating composition. In a preferred formulation of the invention the essential oil concentration is about 0.2 percent. Suitable aromatic additives include geraniole, jasmine base, vanillin, ethyl vanillin, almond extract, lemon oil, lime oil, heliotropin, terpenes, lilac extract, and lavender oil. It will be appreciated that the exact concentration of aromatic material used may be lesser or greater than the range indicated and will be affected by the "strength" of the particular "oil" or the oil mixture selected, and by subjective considerations.

In order to enhance the dispersibility and the solubility of the essential oil in the aqueous system, a surfactant may be incorporated in the composition. The selection of any specific surfactant will be dictated, in part, by the particular essential oil used. In a preferred formulation for practicing the method of the invention, the "non-ionics" are preferred surfactants.

The concentration of the surfactant is conveniently in the range of about 1 percent by weight in the final aqueous solution. Those skilled in the art will understand that the surfactant concentration parameter is in no sense critical. In the light of the teachings herein set forth, persons skilled in the art will be able to make their own formulations including alternative combinations of essential oils and surfactants without the exercise of any inventive faculty, and within the concept of and without departing from the invention itself.

The essence of the present invention is in the use of designated chemical compounds as destroyers of odors, and not in any specific formulation of carrier or diluent composition.

A preferred working formulation used in practicing the method of the invention is set forth below, the relative concentrations being in parts-by-weight.

| | |
|---|---|
| chemical deodorant | 70 |
| essential oil | 7 |
| surfactant | 35 |
| water | 3,600 |

It has been found that the aqueous compositions used in the method of the invention are conveniently prepared in accordance with the following general procedure:

As a first step, the essential oil is mixed with the surfactant. An aliquot, for example, about 10 percent of the total water is then added, with stirring. Thereafter, the remaining water is added in several incremental steps, the mixture being thoroughly stirred after each addition. Finally, the chemical deodorant is added, with stirring, to provide a homogeneous working composition.

Preferably, the water used should be distilled water or "softened" water and should be preheated to a temperature in the range of 110 degrees F. to about 150 degrees F., and preferably 130 degrees F. Lesser or greater concentrations of water, for example, from about 850 to about 70,000 parts by weight, may be used for specific applications.

Treatment of articles or devices in accordance with the invention is carried out conveniently by washing with or by dipping in the chemical deodorant solution. Removal of unpleasant room odors is achieved by distributing the chemical deodorant composition as an air spray. Spills or "accidents" in sick rooms or in examination rooms may be handled similarly. When used with an endoscopic device, a mixture consisting of the deodorizing solution and water (preferably sterile) is substituted for the water normally used. A suitable formulation is one-third to one-half deodorizing solution, and the balance sterile water. It is an important property of the deodorizing composition of the invention that it will not support bacterial growth. Solutions containing the chemical deodorants of the invention appear to be "self-sterilizing."

The invention is claimed as follows:

1. The method of deodorizing fluid and solid media and devices, instruments, appliances, articles and solutions used in connection with analytical, investigative, diagnostic and therapeutic, biological and medical procedures, said method being operative to eliminate odors derived from urine and from fecal matter and residues discharged during the carrying out of medical procedures including procedures using endoscopes and other exploratory and surgical apparatus, and urological, proctoscopic and colonoscopic procedures, said method eliminating the odors through reaction of a chemical deodorant with odor-producing groups and moieties of metabolically-produced odoriferous chemicals present in urine and fecal matter discharged during spills and "accidents" in sick rooms and during the conducting of medical procedures, said method comprising the steps of preparing an aqueous composition containing a chemical agent as a chemical deodorant selected from the group consisting of 2,5-hexanedione, 2,3-pentanedione and mixtures thereof, and applying said composition to a substance to be deodorized.

2. The method as set forth in claim 1 wherein the concentration of said chemical deodorant in said composition is in the range of from about 0.1 percent to about 8 percent by weight.

3. The method as set forth in claim 1 wherein said substance to be deodorized includes medical devices, appliances, and instruments used in connection with an investigative medical procedure and in treating a biological system.

4. The method as set forth in claim 3 wherein the concentration of said chemical deodorant in said composition is in the range of from about 0.1 percent to about 8 percent by weight.

5. The method as set forth in claim 1 including the steps of using an endoscopic device medically, retrieving fluid from a body cavity into which an endoscopic device is introduced, and adding said chemical deodorant to the fluid to deodorize the fluid retrieved from the body cavity.

6. The method as set forth in claim 5 wherein said chemical deodorant is used in a concentration of from about 0.1 percent to about 8 percent by weight in the fluid.

7. The method as set forth in claim 5 including the step of circulating fluid through a body cavity into which the endoscopic device is introduced.

8. The method as set forth in claim 6 including the step of adding said chemical deodorant to the fluid as a dispersant distributed therethrough.

9. The method as set forth in claim 1 and comprising the method of dispelling airborne odors in an ambient environment, said method including the step of dispersing into the air of the ambient environment, as a spray, an aqueous composition containing said chemical agent as a chemical deodorant.

10. The method as set forth in claim 1 herein said chemical deodorant is present in said composition in a concentration in the range of from about 0.1 percent to about 8 percent by weight.

11. The method as set forth in claim 1 wherein said chemical deodorant is 2,5-hexanedione.

12. The method as set forth in claim 1 wherein said chemical deodorant is 2,3-pentanedione.

13. The method as set forth in claim 1 and comprising the method of dispelling airborne odors in an ambient environment, said method including the step of dispersing into the air of the ambient environment, as a spray, an aqueous composition containing 2,5-hexanedione as a chemical deodorant.

14. The method as set forth in claim 1 and comprising the method of dispelling airborne odors in an ambient environment, said method including the step of dispersing into the air of the ambient environment, as a spray, an aqueous composition containing 2,3-pentanedione as a chemical deodorant.

* * * * *